United States Patent [19]
Jenkins et al.

[11] Patent Number: 6,162,910
[45] Date of Patent: Dec. 19, 2000

[54] PROCESS FOR PREPARING LIPOPHILIC OLIGOSACCHARIDE ANTIBIOTICS

[75] Inventors: John K. Jenkins, Chatham; Alan J. Miller, Bridgewater, both of N.J.

[73] Assignee: Schering Corporation, Kenilworth, N.J.

[21] Appl. No.: 09/201,198

[22] Filed: Nov. 30, 1998

[51] Int. Cl.$^7$ ............................ C07H 1/00; A61K 31/715
[52] U.S. Cl. ................. 536/124; 536/18.5; 536/18.7; 536/55.1; 536/55.3; 514/54
[58] Field of Search .................... 536/124, 18.5, 536/18.7, 55.1, 55.3; 514/54

[56] References Cited

U.S. PATENT DOCUMENTS

| | | | |
|---|---|---|---|
| 4,375,361 | 3/1983 | Lyons et al. | 44/310 |
| 5,624,914 | 4/1997 | Patel et al. | 514/54 |
| 5,776,912 | 7/1998 | Patel et al. | 514/54 |

FOREIGN PATENT DOCUMENTS

| | | |
|---|---|---|
| 87 02366 | 4/1987 | WIPO . |
| 93 07904 | 4/1993 | WIPO . |

OTHER PUBLICATIONS

A.K. Ganguly et al., Chemical Modification of Everninomicins, The Journal of Antibiotics, vol XXXV No. 5, (May 1982), pp. 561–570.

S. Kalliney et al., An Efficient Peroxidase–Catalyzed Oxidation of Hydroxylaminoeverninomicin in Aqueous–Organic Media, Tetrahedron Letters, vol. 36, No. 24, (1995), pp. 4163–4166.

*Primary Examiner*—Kathleen K. Fonda
*Attorney, Agent, or Firm*—Joseph T. Maijka; Margaret M. Albanese

[57] ABSTRACT

Process for preparing a lipophilic oligosaccharide antibiotic containing a nitro group using oxidizing agents and catalysts such as cobalt, manganese and copper having an oxidation state of +2 are disclosed.

12 Claims, No Drawings

PROCESS FOR PREPARING LIPOPHILIC OLIGOSACCHARIDE ANTIBIOTICS

BACKGROUND

Orthosomycins are a group of complex lipophilic oligosaccharide antibiotics that are active against gram positive bacteria including methicillin resistant Staphylococci and/or vancomycin resistant Enterococci. Lipophilic oligosaccharide antibiotics include, for example, eveminomicins, the flambamycins, the avilamycins and the curamycins which contain at least one acidic phenolic hydrogen, at least one orthoester linkage associated with carbohydrate residues and usually a nitrogen-containing group. In antibiotics which do possess a nitrogen-containing group or moiety, the most active form of the antibiotic tends to have the nitro ($NO_2$) group. Thus, it would be desirable to provide an efficient process which would provide a lipophilic oligosaccharide antibiotic containing the nitro group or moiety.

SUMMARY OF THE INVENTION

During our studies with these lipophilic oligosaccharide antibiotics, we have discovered an unexpectedly and surprisingly efficient process for providing the oligosaccharide antibiotics.

The present invention is directed toward a process for preparing a lipophilic oligosaccharide antibiotic containing a nitro group or moiety, comprising contacting a lipophilic oligosaccharide antibiotic containing a nitroso (NO), hydroxyamino (NHOH) or amino ($NH_2$) group with
  (i) an oxidizing agent;
  (ii) a catalyst selected from the group consisting of cobalt, manganese or copper having an oxidation state of +2; and
  (iii) an organic solvent;
to give said lipophilic oligosaccharide antibiotic containing a nitro group.

Preferably, the lipophilic oligosaccharide antibiotic containing the nitro group is of the Formula I:

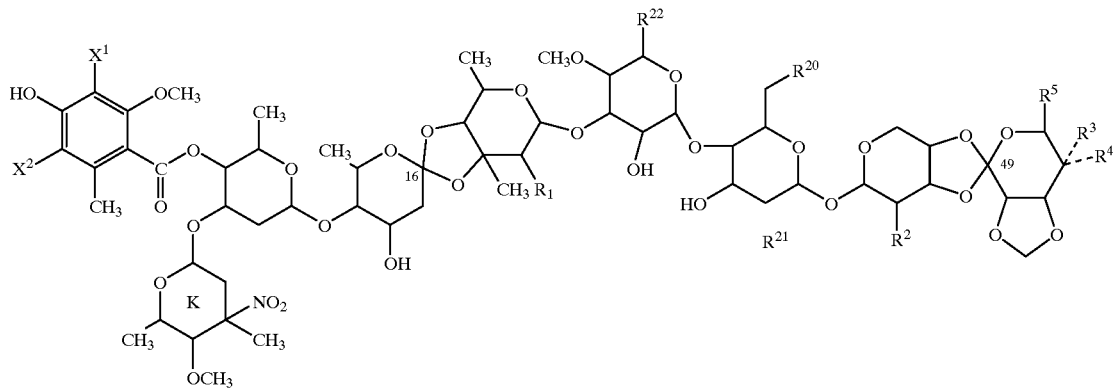

Formula I and the lipophilic oligosaccharide antibiotic containing the nitroso, hydroxyamino or amino group is of the formula II:

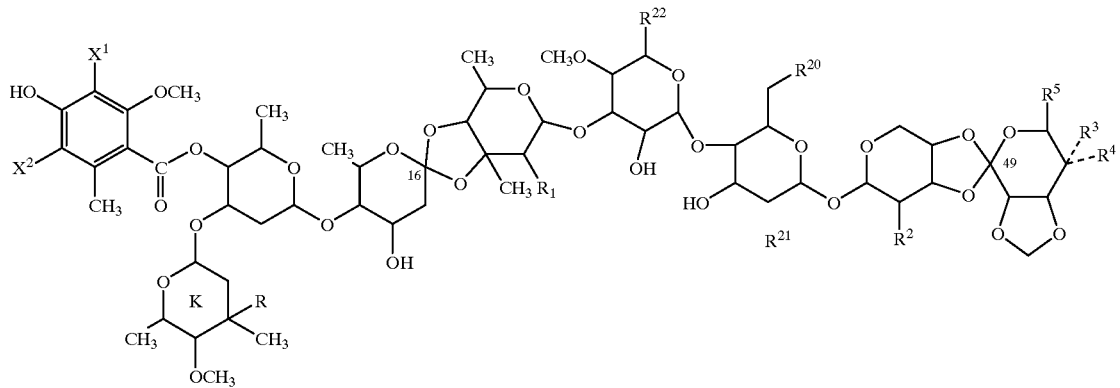

Formula II wherein the lipophilic oligosaccharide antibiotic of formulas I and II, $X^1$ and $X^2$ independently represent hydrogen or chloro, provided at least one of $X^1$ and $X^2$ is chloro;

Ring K is as shown or is hydrogen;

R is —NO, —NHOH or —NH$_2$, $R^1$ is hydrogen or —OH;

$R^2$ is —OH or —OR$^{12}$, wherein $R^{12}$ is alkyl or C(O)R$^{13}$ wherein $R^{13}$ is alkyl;

$R^3$ is hydrogen,

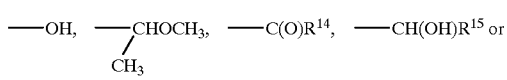

-continued

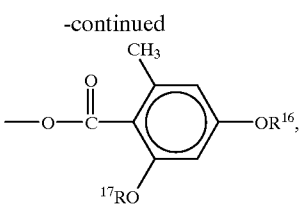

wherein
$R^{14}$ is hydrogen or alkyl,
$R^{15}$ is alkyl,
$R^{16}$ is hydrogen, alkyl or alkenyl,
$R^{17}$ is hydrogen, alkyl or alkenyl,
$R^4$ is hydrogen or OH;
$R^5$ is hydrogen or methyl;
$R^{20}$ is —OH or —OCH$_3$;
$R^{21}$ is —OH or —OCH$_3$; and
$R^{22}$ is hydrogen, —CH$_3$ or —CH$_2$OH.

Also preferred is that the lipophilic oligosaccharide antibiotic of the Formula I containing the nitro group has the stereoconfiguration of Formula I':

Formula I'

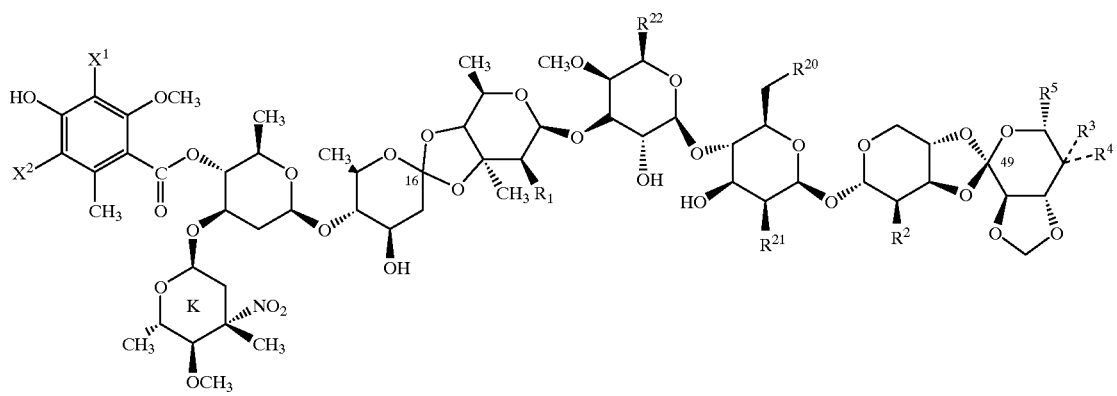

and the lipophilic oligosaccharide antibiotic containing the nitroso, hydroxyamino or amino group has the stereoconfiguration of Formula II':

Formula II'

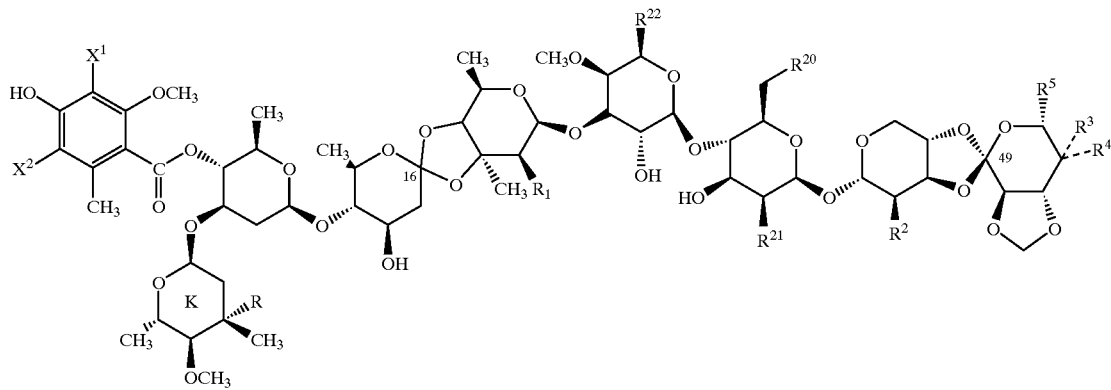

wherein (for either the lipophilic oligosaccharide antibiotic of formulas I' or II'), $X^1$, $X^2$, Ring K, R, $R^1$, $R^2$, $R^3$, $R^4$, $R^5$, $R^{20}$, $R^{21}$ and $R^{22}$ are as defined previously.

Preferably, $X^1$ and $X^2$ are chloro. Preferably, $R^1$ is hydrogen or —OH. Also preferred is that $R^2$ is —OH, —OCH$_3$ or —OCH$_2$CH$_2$OH. Preferably $R^3$ is

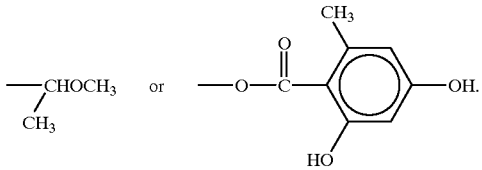

Also preferred is that $R^4$ is hydrogen. Preferably, $R^5$ is hydrogen. Also preferred is that $R^{20}$ and $R^{21}$ are —OCH$_3$ and $R^{22}$ is —CH$_3$.

Optionally, the contacting of ingredients i), ii) and iii) is conducted in the presence of (iv) a base, such as sodium bicarbonate.

One advantage of the present invention is that it provides a process for preparing an oligosaccharide antibiotic containing a nitro group using a catalyst which provides yields as high or even higher than in other known processes using an equivalent amount of catalyst.

A second advantage of the present invention is that it provides a process for preparing an oligosaccharide antibiotic containing a nitro group using catalysts which require lower or fewer "charges (i.e additions)" of catalyst to the reaction mixture compared to other known processes.

A third advantage of the present invention is that it provides a process for preparing an oligosaccharide antibiotic containing a nitro group using less catalyst than from other known processes.

A fourth advantage of the present invention is that it provides a process for preparing an oligosaccharide antibiotic containing a nitro group using catalysts that are less susceptible to deactivation than catalysts from other known processes.

DETAILED DESCRIPTION OF THE INVENTION

The following solvents and reagents are referred to herein by the abbreviations indicated:

tetrahydrofuran (THF);
ethanol (EtOH);
methanol (MeOH);
ethyl acetate (EtOAc);
N,N-dimethylformamide (DMF);
dichloromethane (CH$_2$Cl$_2$);
acetic acid (HOAc or AcOH)
acetoxy or O-acetyl (OAc)

As used herein, the following terms are used as defined below unless otherwise indicated:

◢ or ⋰⋰⋰⋰ indicates the stereoconfiguration of an enantiomer;

- - - - indicates a bond whose stereochemistry can be either in the R or S stereoconfiguration;

Bu—represents butyl;
Et—represents ethyl;
Me—represents methyl;
Ph—represents phenyl;
OMe—represents methoxy.
alkyl—represents straight and branched carbon chains and contains from one to six carbon atoms (i.e. $C_1$–$C_6$); for example methyl, ethyl, propyl, iso-propyl, n-butyl, n-pentyl, isopentyl, hexyl and the like.
alkenyl—represents straight and branched carbon chains having at least one carbon to carbon double bond and containing from 2 to 12 carbon atoms, preferably from 2 to 6 carbon atoms and most preferably from 3 to 6 carbon atoms.
halides—includes, chlorides, bromides, iodides and fluorides.

The terms "lipophilic oligosaccharide antibiotic" and "orthosomycin" are considered substantially synonymous, and refer to a group of complex lipophilic oligosaccharide antibiotics ("antibiotic") that contain at least one acidic phenolic hydrogen; at least one orthoester linkage associated with carbohydrate residues (preferably two orthoester linkages, typically at carbon numbers 16 and 49, i.e. (C16) and (C49)); and usually a nitrogen-containing group, such as nitro, nitroso, hydroxyamino or amino.

Certain oligosaccharide antibiotics of the present invention may exist in different stereoisomeric forms (e.g., enantiomers and diastereoisomers). The invention contemplates all such stereoisomers both in pure form and in mixture, including racemic mixtures.

Certain oligosaccharide antibiotics of formula I, I' or I" will be acidic in nature, e.g. those compounds which possess a carboxyl or phenolic hydroxyl group. These compounds can form pharmaceutically acceptable salts. Examples of such salts may include sodium, potassium, calcium and aluminum salts. Also contemplated are salts formed with pharmaceutically acceptable amines such as ammonia, alkyl amines, hydroxyalkylamines, N-methylglucamine and the like. Methods for preparing such salts are known in the art.

The lipophilic oligosaccharide antibiotic containing a nitro group or moiety can be prepared by contacting a lipophilic oligosaccharide antibiotic containing a nitroso, hydroxyamino or amino group with an oxidizing agent; a catalyst which is a metal salt selected from the group consisting of cobalt, manganese or copper having an oxidation state of +2; and an organic solvent to give said lipophilic oligosaccharide antibiotic containing a nitro group. The process may be illustrated using the lipophilic oligosaccharide antibiotic of formula II as a starting material:

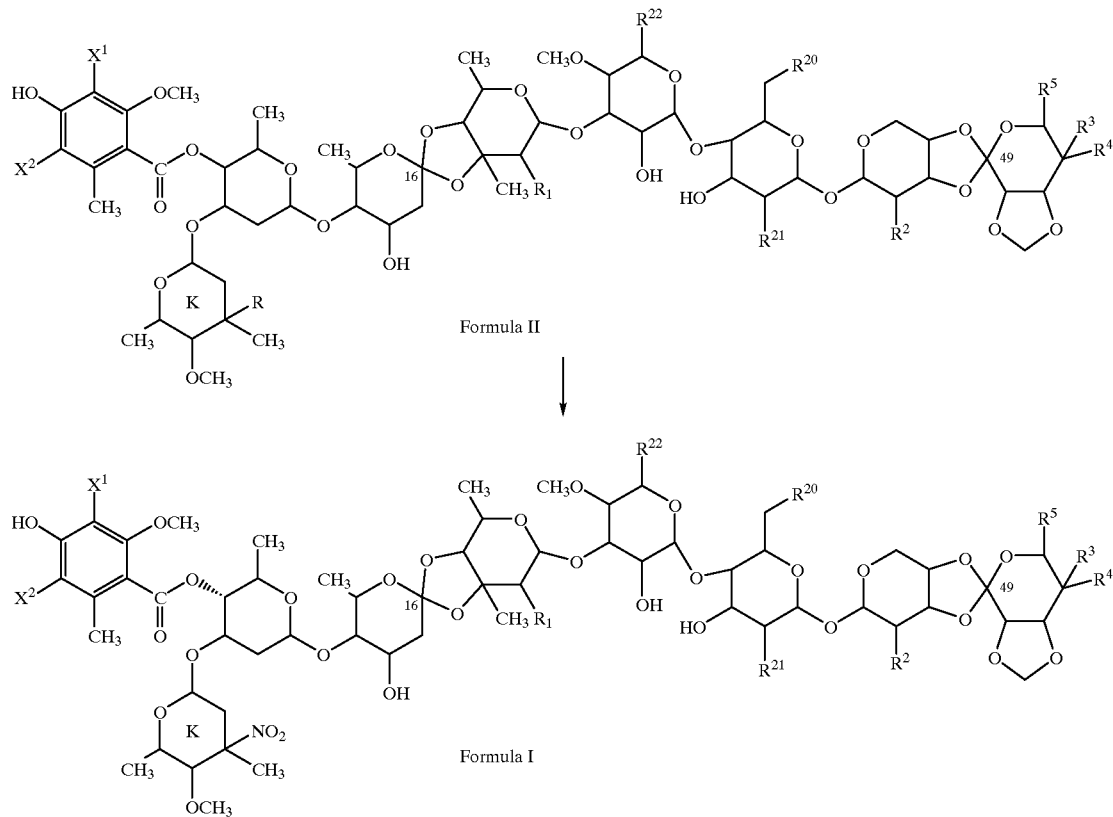
Formula II
Formula I
wherein
$X^1$, $X^2$, Ring K, R, $R^1$, $R^2$, $R^3$, $R^4$, $R^5$, $R^{20}$, $R^{21}$ and $R^{22}$ are as defined previously. The process may also be illustrated using the lipophilic oligosaccharide antibiotic of formula II' as a starting material:
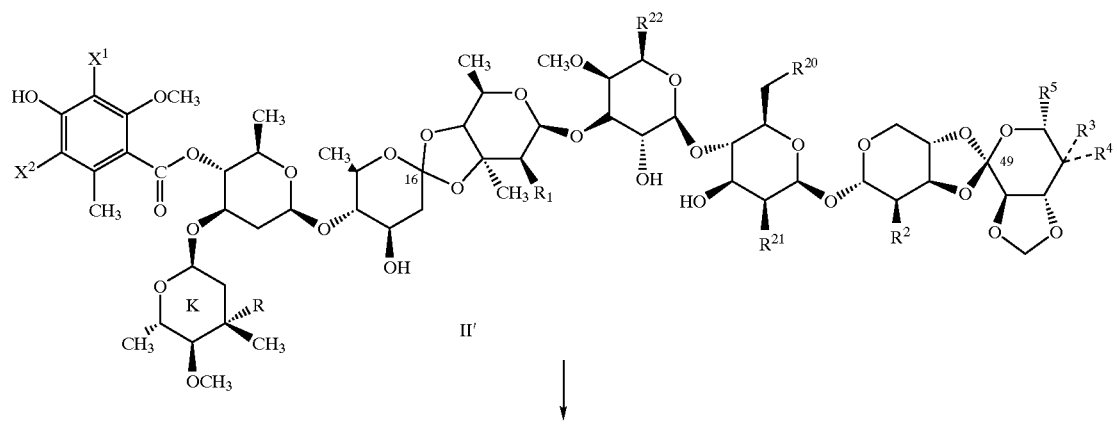
II'

-continued

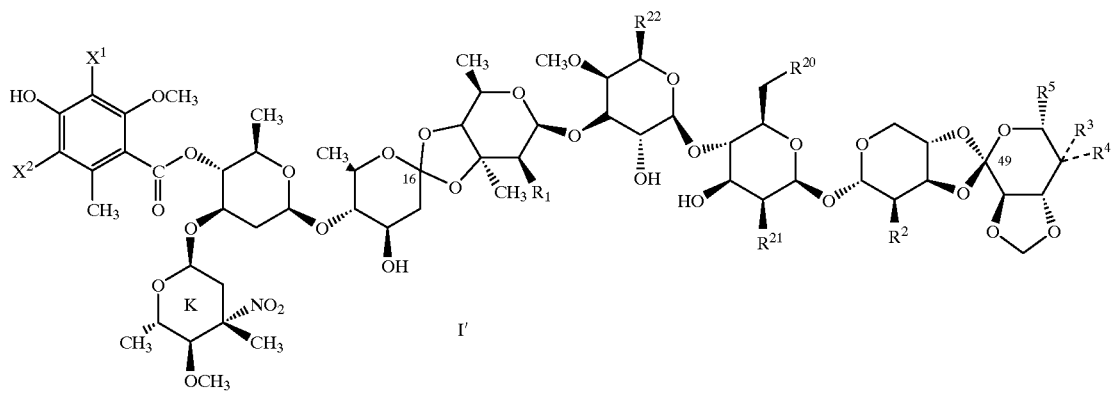

I' wherein $X^1$, $X^2$, Ring K, R, $R^1$, $R^2$, $R^3$, $R^4$, $R^5$, $R^{20}$, $R^{21}$ and $R^{22}$ are as defined previously.

In the above schemes, a crude mixture containing a parent lipophilic oligosaccharide antibiotic of formula II or II' wherein R is $NO_2$, NO, NHOH or $NH_2$ or a mixture thereof, is contacted with an oxidizing agent and a catalyst which is cobalt, manganese or copper having an oxidation state of +2, in the presence of an organic solvent under anhydrous conditions to form the lipophilic oligosaccharide antibiotic of formula I or I'. It should be noted that fermentation broth made of lipophilic oligosaccharide antibiotics may already contain, as part of the antibiotic complex, some antibiotic wherein R is the $NO_2$ (nitro) group. However, even where the antibiotic containing the nitro group is present, the purpose of the present invention is to convert the remaining antibiotics containing other nitrogen-containing "R" groups (i.e. NO, NHOH or $NH_2$) to antibiotics possessing the desired, fully oxidized $NO_2$ group.

Preferably, $R^3$ in lipophilic oligosaccharide antibiotic of formula I and II has the stereoconfiguration.

The oxidizing agent is employed in amounts sufficient to convert the lipophilic oligosaccharide antibiotic containing the nitroso, hydroxyamino or amino group (i.e. of formula II, II' or II") to the lipophilic oligosaccharide antibiotic containing a nitro group (i.e. of formula I, I' or I"). Such amounts can range from about one to excess moles of oxidizing agent per mole of lipophilic oligosaccharide antibiotic containing the nitroso, hydroxyamino or amino group (i.e. of formula II, II' or II"). Generally, more oxidizing agent is needed to convert the hydroxylamino and/or amino groups than the nitroso group. Suitable oxidizing agents include t-butyl hydroperoxide, hydrogen peroxide, ozone, peracids such as peracetic acid, acyl peroxides such as dibenzoyl peroxide and mixtures thereof. Preferably the oxidizing agent is anhydrous (i.e. free of water or aqueous contaminants).

The catalyst employed in the present invention utilizes a cobalt, manganese or copper metal salt having an oxidation state of +2. Suitable catalysts include metal salts such as cobalt(II) acetylacetonate, cobalt(II) acetate, cobalt(II) naphthenate, manganese(II) acetylacetonate, manganese(II) acetate, manganese(II) naphthenate, copper(II) acetylacetonate, copper(II) acetate, copper(II) naphthenate, cobalt halides, manganese halides and copper halides. The catalyst is employed in amount sufficient to catalyze the conversion of the lipophilic oligosaccharide antibiotic containing the nitroso, hydroxyamino or amino group (i.e. of formula II, II' or II") to the lipophilic oligosaccharide antibiotic containing a nitro group (i.e. of formula I, I' or I"). Such amounts of catalyst can range from about 0.001 to about 0.2 moles of catalyst per mole of lipophilic oligosaccharide antibiotic containing the nitroso, hydroxyamino or amino group (i.e. of formula II, II' or II"), more preferably from about 0.002 to about 0.02 moles of catalyst.

The term "oxidation state" or number refers to the number of electrons that must be added to the metal ion, such as cobalt, manganese or copper ion, to reduce the ion to a neutral atom, as defined in R. E. Dickenson, H. B. Gray and G. P. Haight, Jr., Chemical Principles, Chapters 1, 3 and 6, W. A. Benjamin, Inc., Menlo Park, Calif., May 1973, 874 pages. For example, cobalt(II) acetylacetonate indicates a cobalt metal salt having an oxidation state of +2, the number of electrons that must be added to the cobalt metal ion to reduce it to a neutral atom.

The pH of the reaction mixture can range from a pH of about 5 to about 10. Preferably the pH of the reaction medium is neutral or near neutral, i.e a pH from about 6 to about 8.

The reactants are contacted at temperatures sufficient to promote production of the lipophilic oligosaccharide antibiotic containing the nitro group (i.e. of formula I, I' or I"). Such temperatures can range from about 5° C. to about 40° C., preferably from about 150 to about 35° C., more preferably from about 200 to about 30° C.

Preferably, the reactants are agitated during the reaction period using suitable mechanical agitators or stirrers. The reaction can be conducted from about 2 to about 24 hours or more, depending on the temperatures, dilution volumes, catalysts, oxidant concentrations and/or nature of the materials in the reaction mixture.

The reaction can be conducted in the presence of a suitable organic solvent. Suitable organic solvents include aprotic (i.e. not yielding or accepting a proton) solvents such as ethyl acetate, acetonitrile, chloroform, isopropyl acetate, tetrahydrofuran (THF), toluene, methylene chloride, ethers such as ethyl ether or tert-butylmethyl ether, methylisobutyl ketone (MIBK), acetone, alkyl carbonates such as methyl or dimethyl carbonate or mixtures thereof. Preferably the organic solvent has low miscibility with water. Also preferred is that the organic solvent is substantially anhydrous (i.e. free of water). The amount of the organic solvent should be sufficient to dissolve or solubilize the lipophilic oligosaccharide antibiotic containing the nitroso, hydroxyamino or amino group (i.e. of formula II, II' or II") and can range from about four to about 40 volumes (i.e. excess) of solvent per kilogram of the lipophilic oligosaccharide antibiotic of formula II, II' or II". Preferably the amount of solvent can range from about 5 to about 15 volumes of solvent per kilogram of the lipophilic oligosaccharide antibiotic containing the nitroso, hydroxyamino or amino group (i.e. of formula II, II' or II"), more preferably from about 6 to about 12 volumes of solvent.

A base may optionally be employed to neutralize any acids formed during the reaction in the reaction mixture. Suitable bases include carbonates and bicarbonates of alkali and alkaline earth metals, such as calcium carbonate, cesium carbonate, sodium bicarbonate, potassium bicarbonate and lithium bicarbonate. The amount of base can range from about 10% (weight/weight basis) to about 200% (i.e. excess) of the lipophilic oligosaccharide antibiotic containing the nitroso, hydroxyamino or amino group (i.e. of formula II, II' or II"), preferably from about 20 to about 30%.

The lipophilic oligosaccharide antibiotic containing the nitro group (i.e. of formula I, I' or I") can be further processed, recovered or isolated from the reaction mixture by quenching the reaction mixture to reduce excess oxidizing agent present (i.e. peroxide). Optionally, the reaction mixture may be diluted with a suitable organic solvent, such as those previously mentioned, preferably ethyl acetate. Suitable quenching agents for quenching or neutralizing any residual oxidizing agents include aqueous and non-aqueous solutions of sulfites or phosphites, as appropriate. Representative sulfites and phosphites include, for example, sodium bisulfite, diethyl phosphite, sodium hypophosphite and sodium hydrosulfite (sodium dithionite—(NaO)$_2$S$_2$O$_4$·2H$_2$O). Preferably, the sulfite is sodium hydrosulfite. Also preferred is that the sulfite or phosphite is in a buffering agent for adjusting the pH such as potassium phosphate dibasic (K$_2$HPO$_4$). The pH can be adjusted to about 5 and about 10, preferably from about 6 to about 8. The temperature of the mixture can be adjusted to −5 to about 35° C., preferably from about 10 to about 20° C. The quenched mixture can be filtered, optionally in the presence of a filtering aid. Suitable filtering aids include siliceous and/or diatomaceous earths.

The organic/aqueous layers can be separated from the filtering aid plus other insolubles using centrifugation or other filtration procedures. The organic/aqueous filtrate layers can then be separated from the aqueous layer, followed by an optional wash of the organic layer with brine. Brines are typically solutions of sodium chloride and water, usually containing other salts.

The desired lipophilic oligosaccharide antibiotic containing the nitro group (i.e. of formula I, I' or I") can be separated from the organic layer by concentrating the organic layer under vacuum, precipitating the antibiotic by adding the concentrated organic layer to a non-polar solvent, separating the precipitated antibiotic from the organic layer and drying the lipophilic oligosaccharide antibiotic containing the nitro group (i.e. of formula I, I' or I"). Typical non-polar solvents for precipitating the antibiotic include C-6 to C-10 alkanes, branched or unbranched, such as hexane, heptane, octane and the like. The precipitated antibiotic can be separated from the organic layer by filtration, centrifugation and the like; and vacuum dried in an inert atmosphere or under a nitrogen blanket at temperatures ranging from ambient to about 40° C. If desired, the lipophilic oligosaccharide antibiotic containing the nitro group (i.e. of formula I, I' or I") can be further purified using conventional chromatographic procedures.

Oligosaccharide antibiotics of the present invention and preparative starting materials therof, are exemplified by the following examples, which should not be construed as limiting the scope of the disclosure.

EXAMPLE 1

PROCESS FOR PREPARING OLIGOSACCHARIDE ANTIBIOTIC USING A COBALT (II) CATALYST

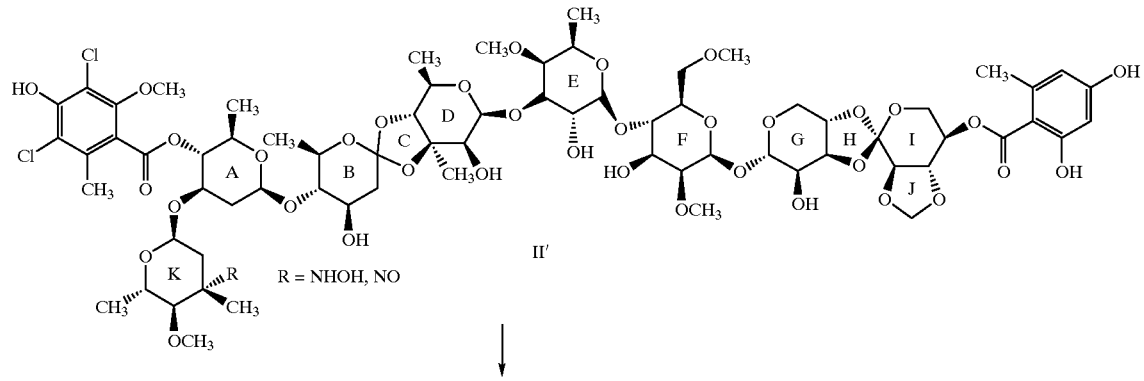

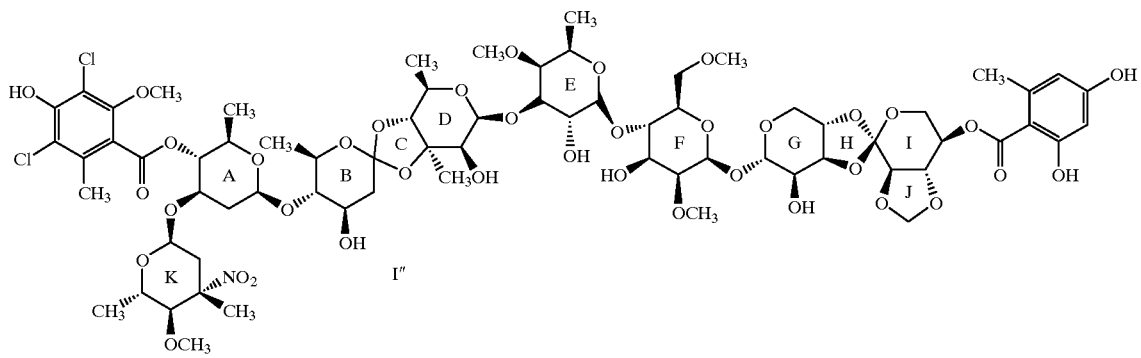

Reaction

To a flask purged with nitrogen gas are added 14 grams (g) of a crude microbial mixture containing a lipophilic oligosaccharide antibiotic of formula II" containing the nitroso and/or hydroxyamino groups, 3.8 g powdered sodium bicarbonate, 56 milligrams (mg) (0.056 g) of cobalt(II) acetylacetonate. The flask is purged with nitrogen gas, 140 milliters (mL) of ethyl acetate are added and the reaction mixture is maintained at a temperature of 24° C. to 25° C. About 4.06 mL of tert-butyl hydroperoxide in decane (5–6 molar solution) are added and the reaction mixture is agitated for about 3 hours or until analysis of the reaction mixture indicates substantial disappearance of the lipophilic oligosaccharide antibiotic II" and the formation of the lipophilic oligosaccharide antibiotic of formula I" containing the desired nitro ($NO_2$) group, giving a yield of 85.7%.

Recovery of Antibiotic I"

The reaction mixture is diluted with 70 mL of ethyl acetate. In a separate flask, a buffered slurry mixture is prepared by mixing 70 mL of water, 12.2 g potassium phosphate dibasic, 4.7 g of sodium hydrosulfite and 2.8 g of siliceous earth. The buffered slurry mixture is slowly added to the flask containing the diluted reaction mixture and the temperature is maintained at a temperature between 15° to 20° C. The combined mixture is filtered to remove the siliceous earth and other insoluble materials. The organic layer is separated from the aqueous layer and washed with a solution of brine prepared from 35 mL of water and 1.4 g of sodium chloride. The washed organic layer is separated from the brine and residual water in the organic layer is removed azeotropically during distillation to a volume of about 60 mL at a temperature of less than 35° C. The concentrated organic layer is added with agitation to a beaker containing about 120 mL of n-heptane to obtain a precipitate of the antibiotic of formula I". The precipitated antibiotic I" is filtered and vacuum dried under a nitrogen flow at ambient temperatures.

EXAMPLE 2

PROCESS FOR PREPARING OLIGOSACCHARIDE ANTIBIOTIC USING MANGANESE (II) CATALYST

Substantially the same procedure is carried out as described in Example 1, except that manganese(II) acetylacetonate is substituted for cobalt(II) acetylacetonate, giving a yield of 81.7%.

EXAMPLE 3

PROCESS FOR PREPARING OLIGOSACCHARIDE ANTIBIOTIC USING COPPER (II) CATALYST

Substantially the same procedure is carried out as described in Example 1, except that copper(II) acetylacetonate is substituted for cobalt(II) acetylacetonate, giving a yield of 84.2%.

PREPARATION OF STARTING MATERIALS

The lipophilic oligosaccharide antibiotic containing the nitroso, hydroxyamino or amino group (i.e. of formula II, II' or II") are useful starting materials for preparing the lipophilic oligosaccharide antibiotic containing the nitro group (i.e. of formula I, I' or I") are known in the art and/or can be prepared using known methods, such as taught, for example, U.S. Pat. Nos. 4,597,968; 4,735,903; 5,624,914; and 5,763,600; in A. K. Ganguly et al., The Structure of New Oligosaccharide Antibiotics, 13-384 Components 1 and 5, Heterocycles, Vol. 28, No. 1, (1989), pp. 83–88; in A. K. Ganguly et al., Chemical Modification of Eveminomicins, The Journal of Antibiotics, Vol. XXXV No. 5, (1982), pp. 561–570; and V. M. Girijavallabhan & A. K. Ganguly, Kirk-Othmer Encyclopedia of Chemical Technology, 4th Ed., Vol. No. 3, (1992) pp. 259–266, Derek E. Wright, Tetrahedron Report Number 62, The Orthosomycins a New Family of Antibiotics, Tetrahedron Vol. 35, Pergamon Press Ltd., (1979), pp 1207–1237; in A. Saksena et. al., Structure Elucidation of SCH49088, A Novel Eveminomicin Antibiotic Containing An Unusual Hydroxylamino-ether Sugar, Everhydroxylaminose, Tetrahedron Letters, 39 (1998), pages 8441–8444; and in references cited therein. For example, U.S. Pat. No. 5,624,914 discloses that the the nitroso analog of a lipophilic oligosaccharide was converted into the nitro compound of formula III (the same antibiotic as the lipophilic oligosaccharide antibiotic of formula I" in the present specification) by use of an oxidizing agent such as tertiary butyl hydroperoxide (t-$BuO_2H$) with vanadyl acetylacetonate dissolved in an aprotic solvent at room temperature. Everninomicin-type antibiotics are components from cultures of *Micromonospora carbonaceae*. For example, certain everninomicin type compounds of formula I" can be prepared from typical fermentation of *Micromonospora carbonacea* var. *africana*, NRRL 15099, ATCC39149 or higher yielding subspecie thereof. For example, one subspecies, strain PF6-3, is prepared from the parent strain ATCC39149, by reisolations and treatments with ultraviolet light (UV) and N-methyl-N'-nitro-N-nitrosoguanidine (MNNG or NTG). Flambamycins are produced by *Streptomyces hygroscopicus*. Curamycin A is the p rimary component in the culture of *Streptomyces curacoi*. Avilamycins are the primary components produced by the species *Streptomyces viridochromgenes*.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for preparing a lipophilic oligosaccharide antibiotic containing a nitro group, comprising contacting a lipophilic oligosaccharide antibiotic containing a nitroso (NO), hydroxyamino (NHOH) or amino ($NH_2$) group with (i) an oxidizing agent;

(ii) a catalyst selected from the group consisting of cobalt(II) acetylacetonate or manganese (II) acetylacetonate; and (iii) an organic solvent.

2. The process of claim 1 wherein said lipophilic oligosaccharide antibiotic containing a nitro group is of the formula I:

Formula I

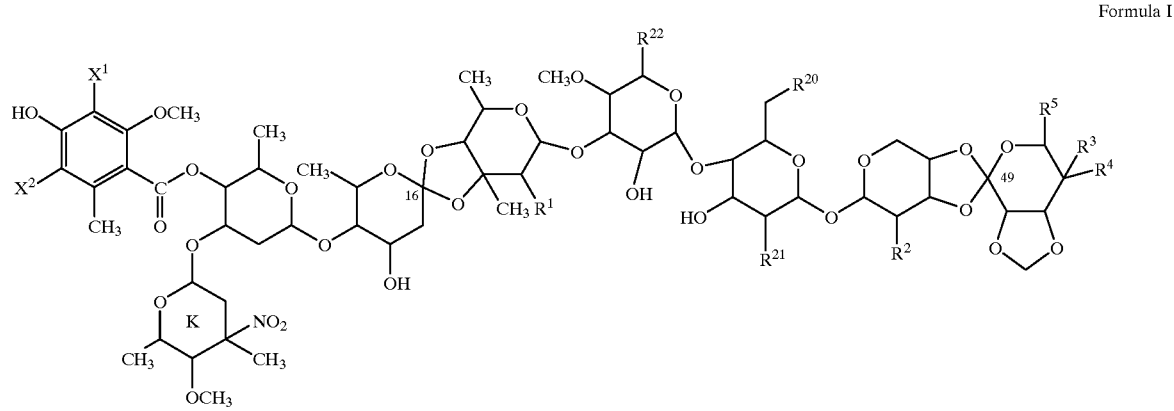

and said lipophilic oligosaccharide antibiotic containing the nitroso, hydroxyamino or amino group is of the formula II:

Formula II

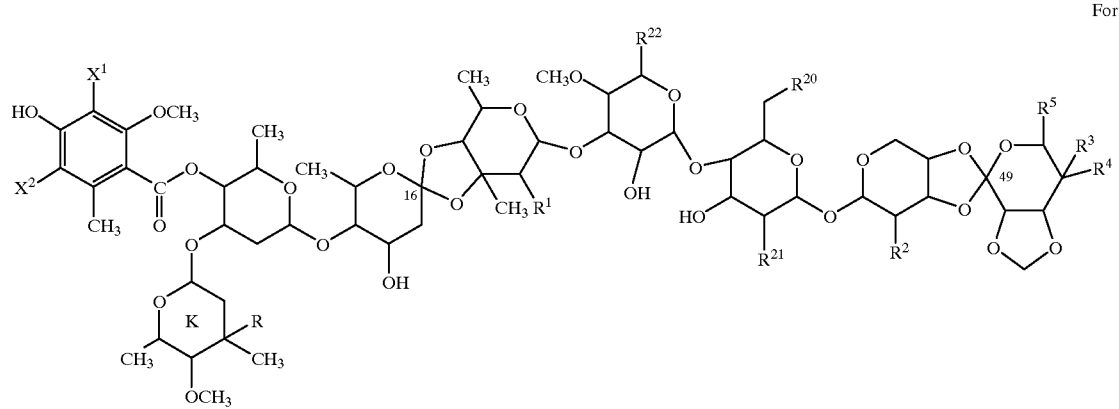

wherein in the lipophilic oligosaccharide antibiotic of formulas I and II,

X$^1$ and X$^2$ independently represent hydrogen or chloro, provided at least one of X$^1$ and X$^2$ is chloro;

Ring K is as shown or is replaced by hydrogen;

R is —NO, —NHOH or —NH$_2$,

R$^1$ is hydrogen or —OH;

R$^2$ is —OH or —OR$^{12}$, wherein

R$^{12}$ is alkyl or C(O)R$^{13}$ wherein R$^{13}$ is alkyl;

R$^3$ is hydrogen,

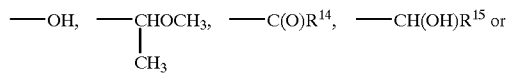

-continued

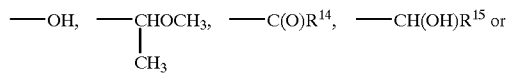

wherein
R$^{14}$ is hydrogen or alkyl,
R$^{15}$ is alkyl,
R$^{16}$ is hydrogen, alkyl or alkenyl,
R$^{17}$ is hydrogen, alkyl or alkenyl,
R$^4$ is hydrogen or OH;
R$^5$ is hydrogen or methyl;
R$^{20}$ is —OH or —OCH$_3$;
R$^{21}$ is —OH or —OCH$_3$; and
R$^{22}$ is hydrogen, —CH$_3$ or —CH$_2$OH.

3. The process of claim 1 wherein said lipophilic oligosaccharide antibiotic containing a nitro group is of the formula I':

Formula I'

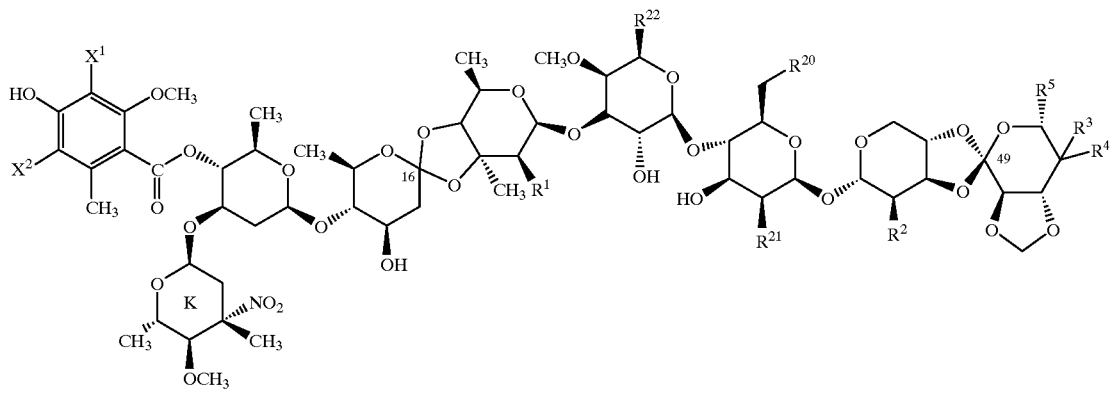

and said lipophilic oligosaccharide antibiotic containing the nitroso, hydroxyamino or amino group is of the Formula II':

Formula II'

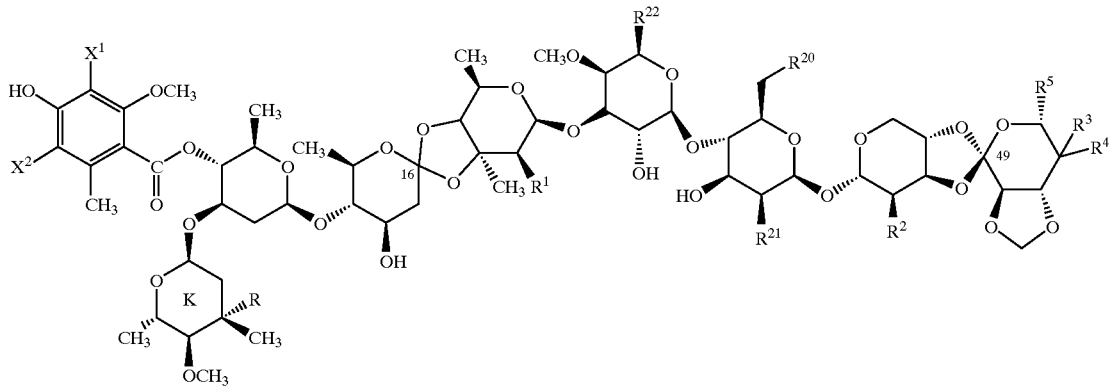

wherein in the lipophilic oligosaccharide antibiotic of formulas I' and II',

X¹ and X² independently represent hydrogen or chloro, provided at least one of X¹ and X² is chloro;

Ring K is as shown or is replaced by hydrogen;

R is —NO, —NHOH or —NH$_2$, $R^1$ is hydrogen or —OH;

$R^2$ is —OH or $OR^{12}$, wherein $R^{12}$ is alkyl or $C(O)R^{13}$ wherein $R^{13}$ is alkyl;

$R^3$ is hydrogen,

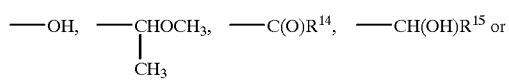

-continued

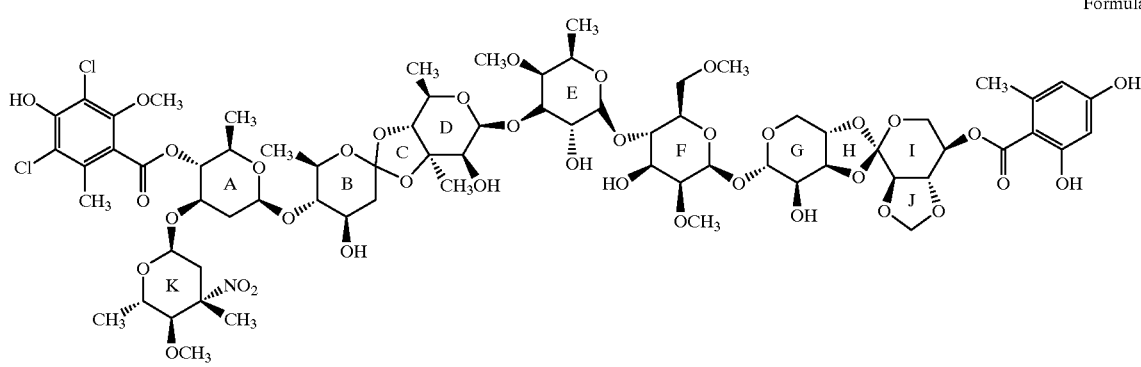

wherein
$R^{14}$ is hydrogen or alkyl,
$R^{15}$ is alkyl,
$R^{16}$ is hydrogen, alkyl or alkenyl,
$R^{17}$ is hydrogen, alkyl or alkenyl,
$R^4$ is hydrogen or OH,
$R^5$ is hydrogen or methyl;
$R^{20}$ is —OH or —OCH$_3$;
$R^{21}$ is —OH or —OCH$_3$; and
$R^{22}$ is hydrogen, —CH$_3$ or —CH$_2$OH.

4. The process of claim 1 wherein said lipophilic oligosaccharide antibiotic containing a nitro group is of the formula I":

Formula I"

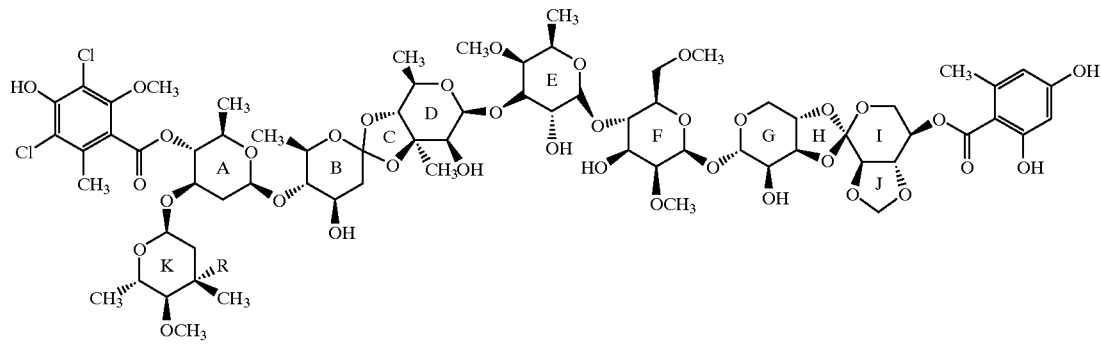

and said lipophilic oligosaccharide antibiotic containing the nitroso, hydroxyamino or amino group is of the formula II":

Formula II"

wherein R is —NO or —NHOH.

5. The process of claim 1 wherein said oxidizing agent is tert-butyl hydroperoxide.

6. The process of claim 1 wherein said oxidizing agent is tert-butyl hydroperoxide and said said catalyst is cobalt(II) acetylacetonate.

7. The process of claim 1 wherein said solvent is ethyl acetate.

8. The process of claim 1 wherein said oxidizing agent is tert-butyl hydroperoxide, said catalyst is cobalt(II) acetylacetonate and said solvent is ethyl acetate.

9. The process of claim 1 wherein said oxidizing agent is tert-butyl hydroperoxide and said said catalyst is manganese (II) acetylacetonate.

10. The process of claim 1 wherein said oxidizing agent is tert-butyl hydroperoxide, said catalyst is manganese (II) acetylacetonate and said solvent is ethyl acetate.

11. The process of claim 1 further comprising contacting said lipophilic oligosaccharide antibiotic containing a nitroso (NO), hydroxyamino (NHOH) or amino ($NH_2$) group with a base.

12. The process of claim 11 wherein said base is sodium bicarbonate.

* * * * *